United States Patent [19]
Hui

[11] Patent Number: 5,513,236
[45] Date of Patent: Apr. 30, 1996

[54] IMAGE RECONSTRUCTION FOR A CT SYSTEM IMPLEMENTING A DUAL FAN BEAM HELICAL SCAN

[75] Inventor: Hu Hui, Waukesha, Wis.

[73] Assignee: General Electric Company, Milwaukee, Wis.

[21] Appl. No.: 376,829

[22] Filed: Jan. 23, 1995

[51] Int. Cl.⁶ .................................................. A61B 6/03
[52] U.S. Cl. ....................... 378/15; 378/901; 364/413.17
[58] Field of Search ................................ 378/4, 15, 901; 364/413.17

[56] References Cited

U.S. PATENT DOCUMENTS

| | | | |
|---|---|---|---|
| 4,580,219 | 4/1989 | Pelc et al. | 364/413.21 |
| 4,821,210 | 4/1989 | Rumbaugh | 395/121 |
| 5,047,931 | 9/1991 | Lin | 364/413.21 |
| 5,233,518 | 8/1993 | King et al. | 364/413.18 |
| 5,253,171 | 10/1993 | Hsiao et al. | 364/413.19 |
| 5,262,946 | 11/1993 | Heuscher | 364/413.18 |
| 5,265,142 | 11/1993 | Hsieh | 378/4 |
| 5,270,923 | 12/1993 | King et al. | 364/413.13 |

OTHER PUBLICATIONS

Crawford et al., Computed Tomography Scanning with Simultaneous Patient Translation, Med. Phys. 17(6), Nov./Dec. 1990, pp. 967–982.

Primary Examiner—David P. Porta
Assistant Examiner—David Vernon Bruce
Attorney, Agent, or Firm—John S. Beulick; John H. Pilarski

[57] ABSTRACT

The present invention, in one form, is an apparatus for performing image reconstruction using data obtained by a dual beam helical scan. In reconstructing an image in accordance with the present invention, projection data from each fan beam measurement is weighted by weighting factors to obtain a reconstructed slice. The data arrays selected and weighting factors applied vary depending on the table speed and the detector spacing measured at the axis of gantry rotation, i.e., the detector z spacing.

18 Claims, 10 Drawing Sheets

IMAGE RECONSTRUCTION FOR A CT SYSTEM IMPLEMENTING A DUAL FAN BEAM HELICAL SCAN

FIELD OF THE INVENTION

This invention relates generally to computed tomography (CT) imaging and more particularly, to the reconstruction of images from data acquired from a helical scan using dual fan beams.

BACKGROUND OF THE INVENTION

In CT systems, an x-ray source projects a fan-shaped beam which is collimated to lie within an X-Y plane of a Cartesian coordinate system, termed the "imaging plane". The x-ray beam passes through the object being imaged, such as a patient, and impinges upon a linear array of radiation detectors. The intensity of the transmitted radiation is dependent upon the attenuation of the x-ray beam by the object. Each detector of the linear array produces a separate electrical signal that is a measurement of the beam attenuation. The attenuation measurements from all the detectors are acquired separately to produce a transmission profile.

The x-ray source and the linear detector array in a CT system are rotated with a gantry within the imaging plane and around the object so that the angle at which the x-ray beam intersects the object constantly changes. A group of x-ray attenuation measurements from the detector array at one gantry angle is referred to as a "view". A "scan" of the object comprises a set of views made at different gantry angles during one revolution of the x-ray source and detector. In an axial scan, data is processed to construct an image that corresponds to a two dimensional slice taken through the object. One method for reconstructing an image from a set of data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved while the data for the prescribed number of slices is acquired. A dual beam helical scan may be used to even further reduce the total scan time. Such a scan is made by utilizing a CT system in which two rows of detectors, displayed along the axis of gantry rotation simultaneously collect projection measurements at different axial locations. These two detector rows define two fan beams. In helical scanning, such a system generates interwoven double helixes, as opposed to a single helix from a conventional fan beam helical scan. The interwoven double helixes mapped out by the two fan beams yield projection data from which images in each prescribed slice may be reconstructed with reduced image degradation due to patient translation.

It is desirable, of course, to reconstruct images from the data obtained in a dual beam helical scan in a manner which provides a high quality image with a minimum level of artifacts. It also is desirable to reduce the total time required to reconstruct such an image.

SUMMARY OF THE INVENTION

The present invention, in one form, includes apparatus for performing image reconstruction using data obtained by a dual beam helical scan. More particularly, in accordance with the one form of the present invention, projection space data arrays are selected from projection data acquired by each fan beam. Data in each array is then weighted to correct for the translational motion of the patient and to offset data redundancy affects. An image is then reconstructed using the weighted data.

More specifically, and as described hereinafter in detail, the present invention is, in one form, an algorithm which, in reconstructing an image, generates projection data arrays corresponding to data planes associated with the slice to be imaged. Weighting factors are then applied to the data arrays assign a weight to each particular data element. The data arrays selected and weighting factors applied vary depending on the table speed and the detector spacing at the axis of gantry rotation, i.e., the detector z spacing. The present invention provides reconstruction of a high quality image slice, and reduces the total time required to reconstruct such an image.

DETAILED DESCRIPTION OF THE DRAWINGS

Figure 1:
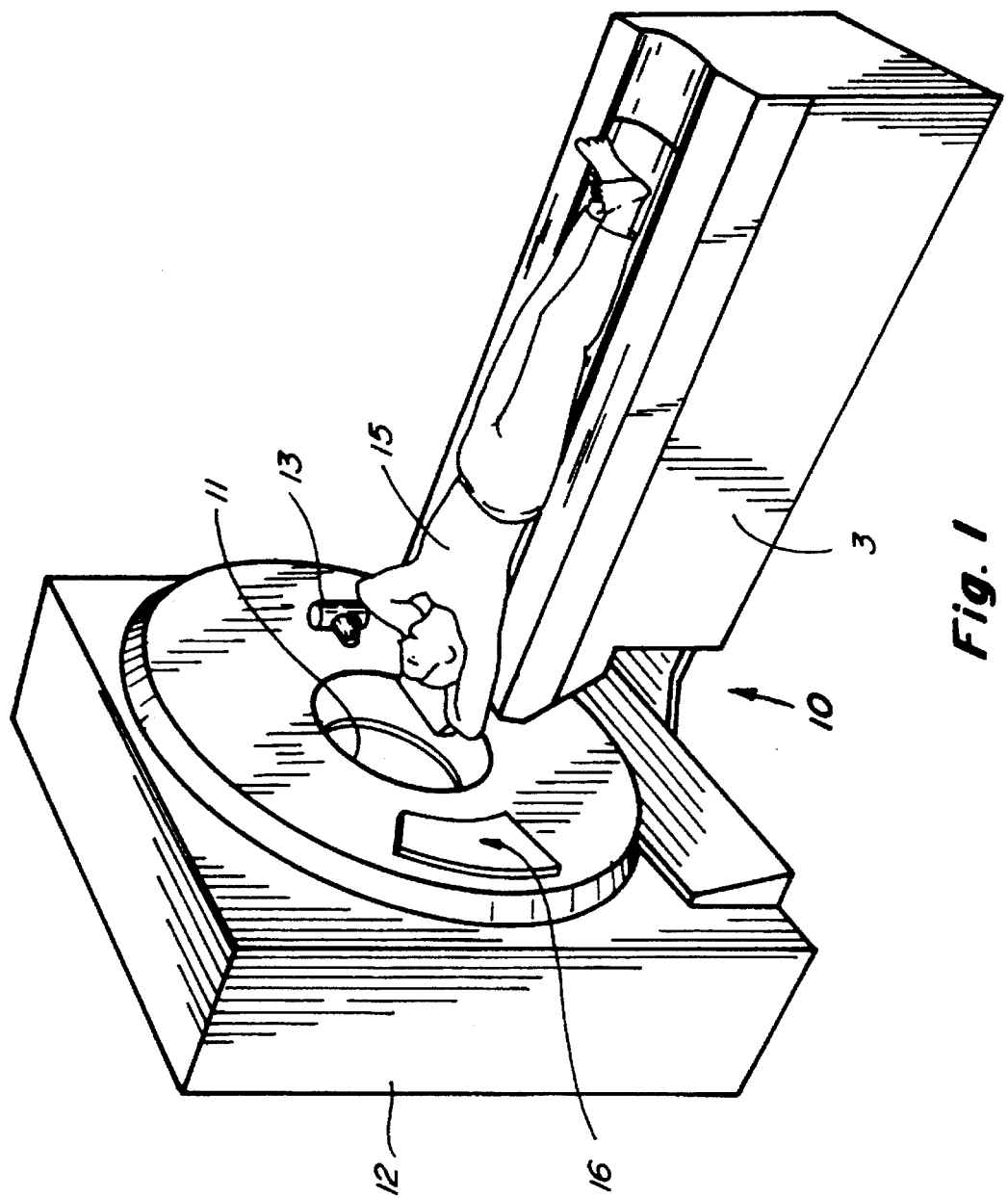
FIG. 1 is a pictorial view of a CT imaging system in which the present invention may be employed.
Figure 2:
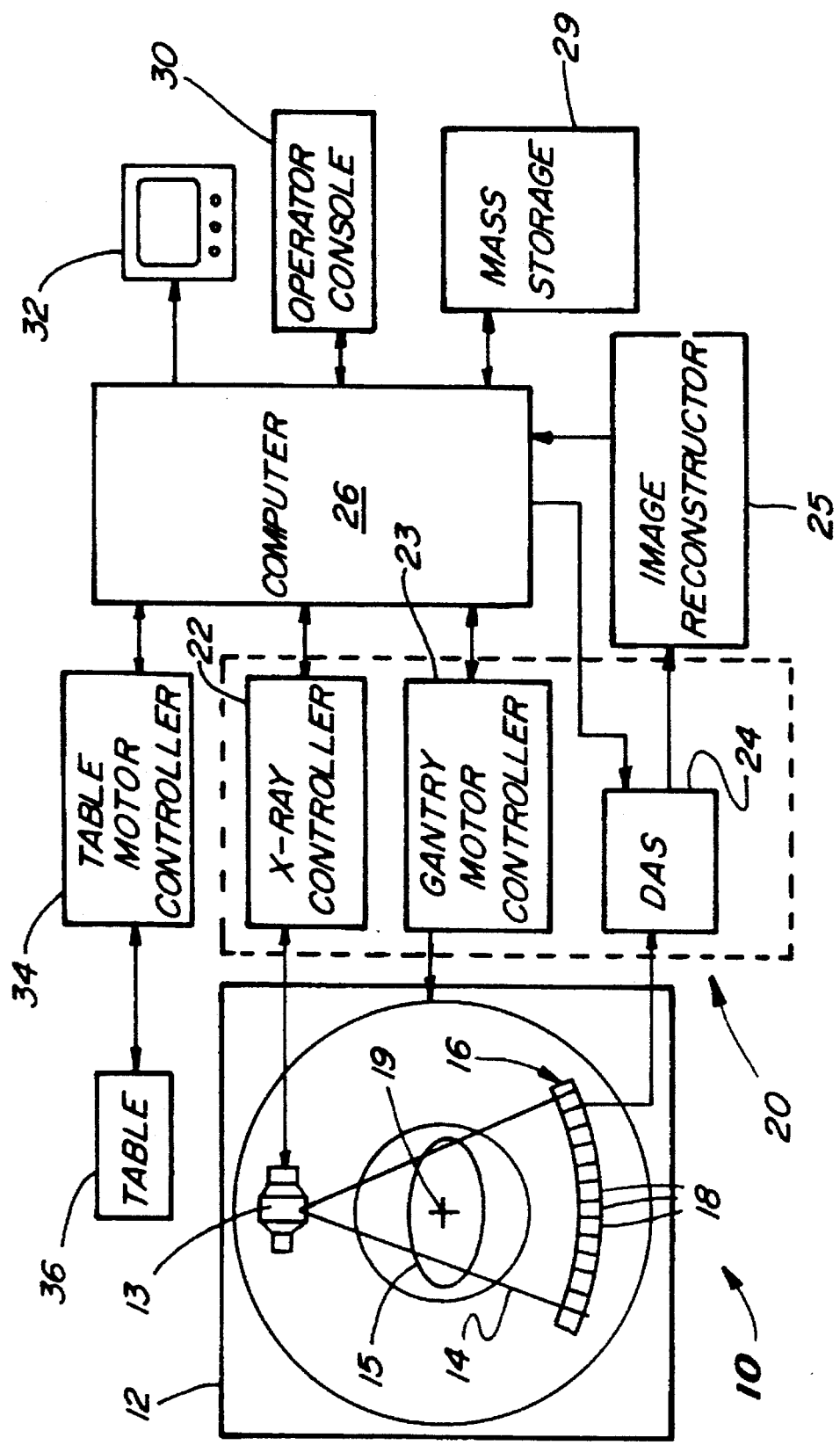
FIG. 2 is a block schematic diagram of the CT imaging system illustrated in FIG. 1.

With reference to FIGS. 1 and 2, a computed tomography (CT) imaging system 10 includes a gantry 12 representative of a "third generation" CT scanner. Gantry 12 has an x-ray source 13 that projects a beam of x-rays 14 toward a detector array 16 on the opposite side of gantry 12. Detector array 16 is formed by two rows of detector elements 18 which together sense the projected x-rays that pass through a medical patient 15. Each detector element 18 produces an electrical signal that represents the intensity of an impinging x-ray beam and hence the attenuation of the beam as it passes through patient 15. During a scan to acquire x-ray projection data, gantry 12 and the components mounted thereon rotate about a center of rotation 19.

Rotation of gantry 12 and the operation of x-ray source 13 are governed by a control mechanism 20 of CT system 10. Control mechanism 20 includes an x-ray controller 22 that provides power and timing signals to x-ray source 13 and a gantry motor controller 23 that controls the rotational speed and position of gantry 12. A data acquisition system (DAS) 24 in control mechanism 20 samples analog data from detector elements 18 and converts the data to digital signals for subsequent processing. An image reconstructor 25 receives sampled and digitized x-ray data from DAS 24 and performs high speed image reconstruction. The reconstructed image is applied as an input to a computer 26 which stores the image in a mass storage device 29.

Computer 26 also receives commands and scanning parameters from an operator via console 30 that has a keyboard. An associated cathode ray tube display 32 allows the operator to observe the reconstructed image and other data from computer 26. The operator supplied commands and parameters are used by computer 26 to provide control signals and information to DAS 24, x-ray controller 22 and gantry motor controller 23. In addition, computer 26 operates a table motor controller 34 which controls a motorized table 36 to position patient 15 in gantry 12.

Figure 3:
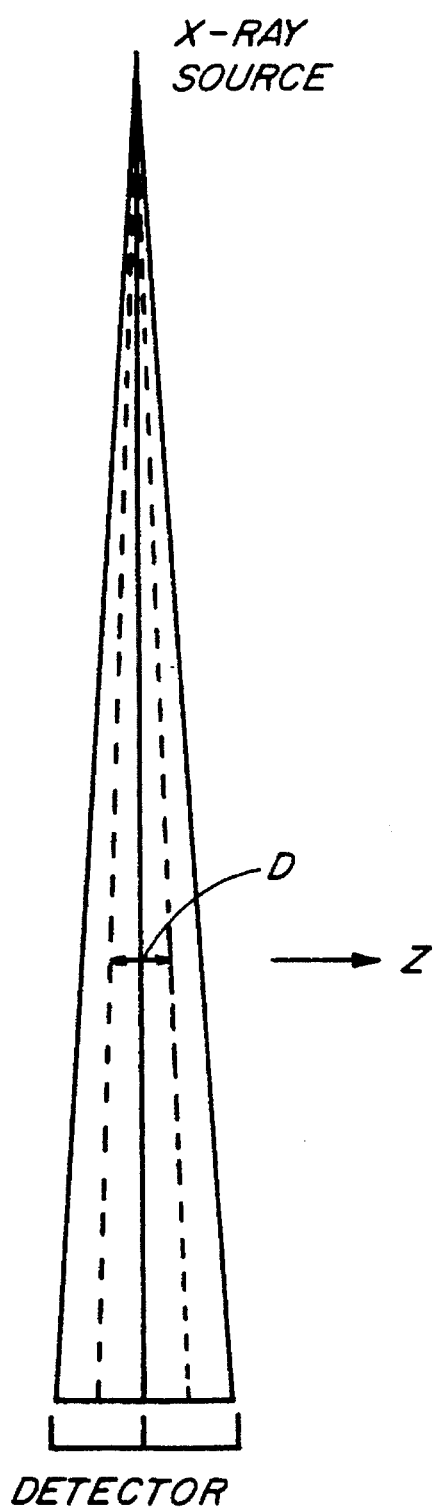
FIG. 3 is a schematic representation of dual, x-ray fan beam in cross section along the x-axis.

As shown in FIG. 3, two rows of detectors are employed in a dual fan beam system. The x-ray fan beam is, in effect, split into two fan beams, displaced along the z-axis of rotation. If the two fan beams are denoted as the front and back beam, the distance between the center of these two beams is D when measured at the axis of gantry rotation.

Figure 4:
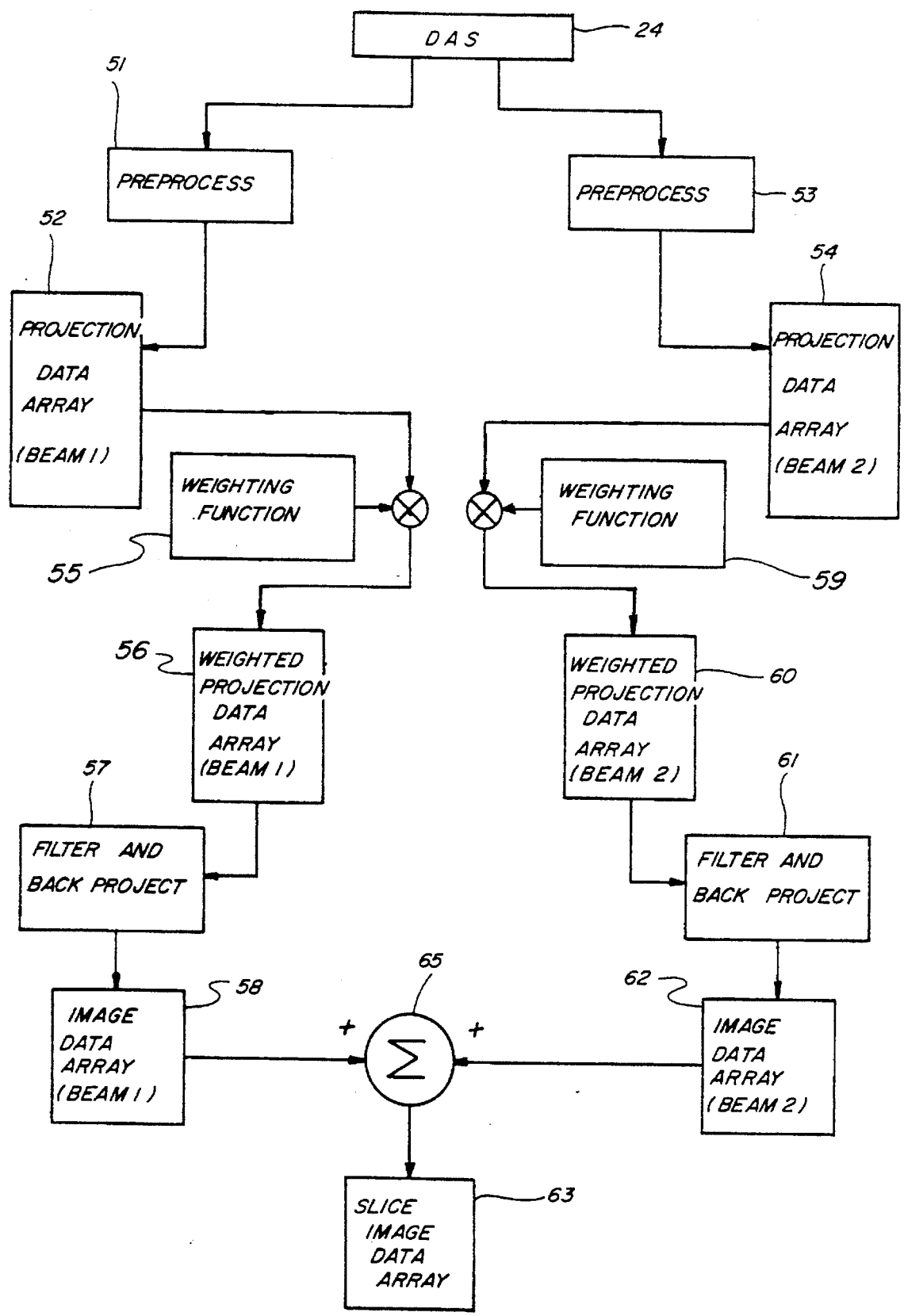
FIG. 4 is a block diagram of an image reconstructor which forms part of the CT imaging system of FIG. 2.

Image reconstructor 25 is shown in more detail in FIG. 4. Each view of data from DAS 24 for the first fan beam is received at preprocess 51 where it is preprocessed to correct for various well-known errors such as beam hardening, offsets and variations in detector and channel gain. Also, the negative logarithm is taken to provide projection data which is stored in a projection data array 52. The same preprocessing is applied to the second fan beam scan data at preprocess 53 and the data is stored in a projection data array 54. The projection data stored in arrays 52 and 54 is combined, as hereinafter described, to produce a slice image.

The projection data in beam 1 array 52 is read out and the corresponding weighting function 55 is applied. The weighted projection data is written into the corresponding location in an array 56, and this weighted projection data is filtered and back projected 57 to produce a beam 1 image data array 58. Similarly, the corresponding data set of beam 2 is read out of array 54 and the corresponding weighting function 59 is applied. The resulting weighted projection data array 60 is filtered and back projected 61 to produce a second beam image data array 62.

A slice image data array 63 is produced by combining two image arrays 58 and 62. This is accomplished by summer 65 which adds the magnitude of each pixel in beam 1 array 58 with the magnitude of the corresponding pixel in beam 2 array 62. The resulting slice image array 63 may be stored for later use or displayed to the operator. As described hereinafter, and rather than summing the data subsequent to generation of image data arrays 58 and 62, the projections from the same gantry (view) angle but from different detector rows can be combined prior to filtering and back projecting the data. Such a combination reduces the processing load.

The present invention, in one form, relates specifically to the creation of weighted projection data arrays 56 and 60 when the dual beam scan has been performed under certain predetermined conditions. With respect to the following discussion describing various forms of the present invention in detail, d denotes the detector row (the z) spacing measured at the axis of the gantry rotation, s denotes the table feeding speed (per rotation), and p denotes the ratio of d and s, that is:

$$p = d/s. \tag{1}$$

Figure 5A:
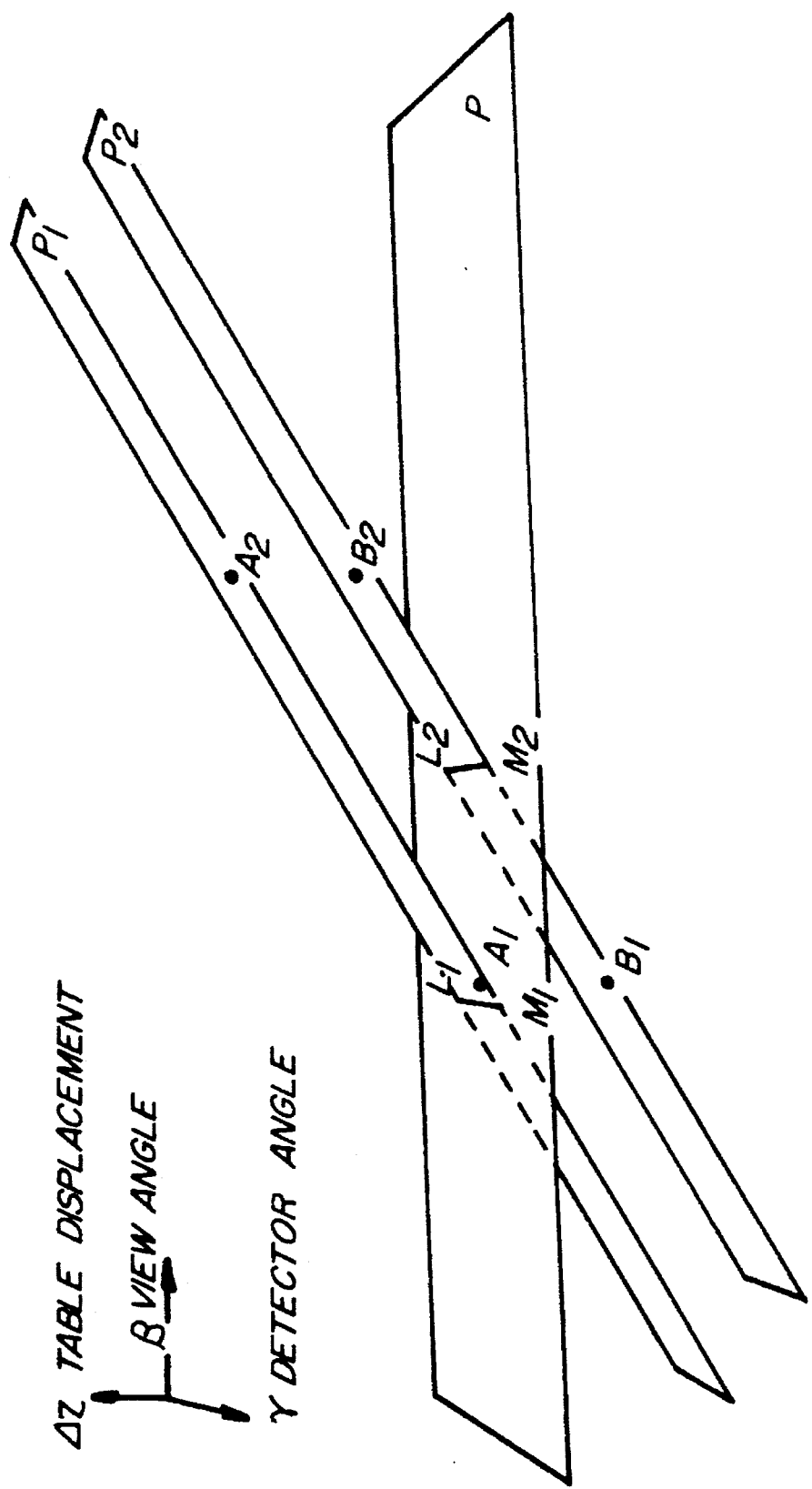
FIG. 5a illustrates the intersection of two data planes with an image slice and FIG. 5b illustrates the relationship between the gantry angle and the fan beam angle.

As shown in FIG. 5a, data planes $P_1$ and $P_2$ intercept slice P to be reconstructed at lines $L_1M_1$ and $L_2M_2$. These line functions can be expressed as:

$$L_1M_1: \beta1 = -p\pi, \text{ and} \tag{2}$$
$$L_2M_2: \beta2 = p\pi,$$

where $\beta$ is equal to the gantry angle. Lines $L_1M_1$ and $L_2M_2$ have two sets of "mirror" lines, denoted as + and − sets as follows:

$$\beta 1_\pm = -p\pi \pm \pi - 2\gamma, \text{ and} \tag{3}$$
$$\beta 2_\pm = p\pi \pm \pi - 2\gamma,$$

where $\gamma$ is equal to the detector angle.

Furthermore, given that gantry angle $\beta$ is a periodical function with a period of $2\pi$, the following relationships exist:

$$\beta 1_{\pm 2\pi} = -p\pi \pm 2\pi \tag{4}$$
$$\beta 2_{\pm 2\pi} = p\pi \pm 2\pi.$$

Figure 5B:
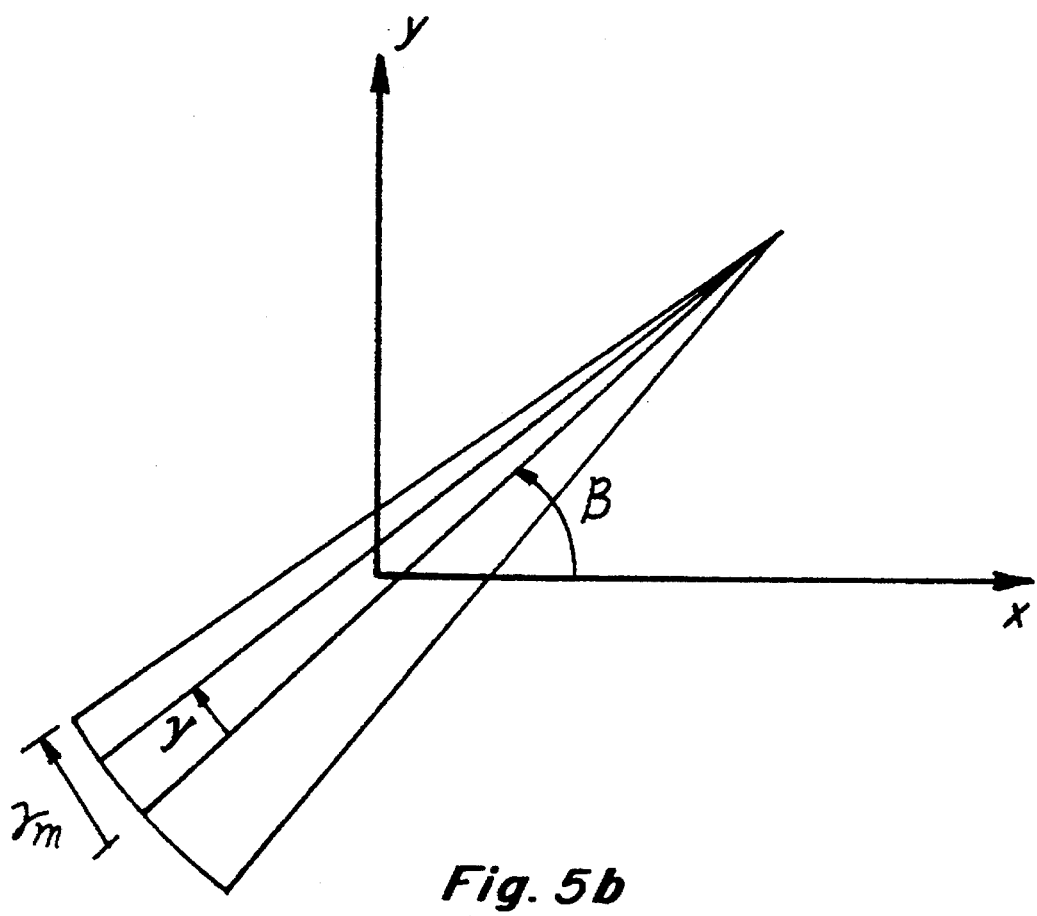

In accordance with the present invention, and when the table feeding speed s and the detector z spacing, d, satisfy the relation $d < s < (2\pi/(\pi + 2\gamma_m))d$, where $\gamma_m$ is defined as half of the fan angle (see FIG. 5b), the helical weighting factor to be applied for each data set, denoted as W1 $(\beta,\gamma)$ and W2 $(\beta, \gamma)$, are:

$$W1(\beta,\gamma) = \begin{cases} 0 & \beta \leq \beta2_{-2\pi} \\ \dfrac{\beta - \beta2_{-2\pi}}{\beta1 - \beta2_{-2\pi}} & \beta2_{-2\pi} < \beta \leq \beta1 \\ \dfrac{\beta - \beta2_-}{\beta1 - \beta2_-} & \beta1 < \beta < \beta2_- \\ 0 & \beta \geq \beta2_- \end{cases} \tag{5}$$

$$W2(\beta,\gamma) = \begin{cases} 0 & \beta \leq \beta1_+ \\ \dfrac{\beta - \beta1_+}{\beta2 - \beta1_-} & \beta1_+ < \beta \leq \beta2 \\ \dfrac{\beta - \beta1_{+2\pi}}{\beta2 - \beta1_{-2\pi}} & \beta2 \leq \beta < \beta1_{+2\pi} \\ 0 & \beta \geq \beta1_{+2\pi} \end{cases} \tag{5}$$

Figure 6:
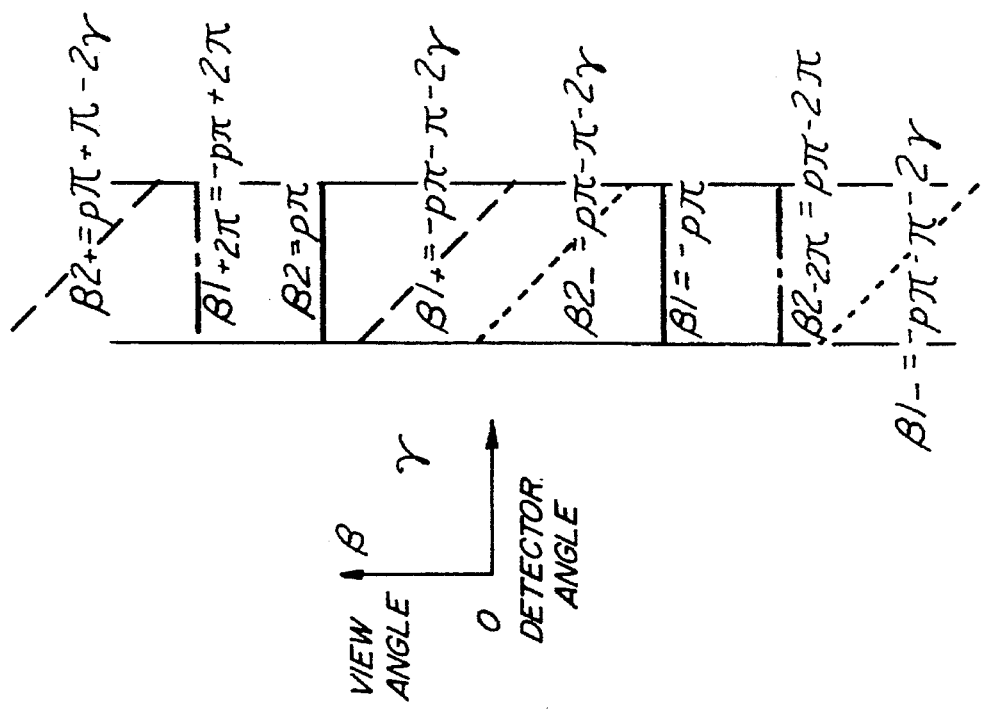
FIG. 6 illustrates a data plane and various data regions for a first set of conditions.
Figure 7:
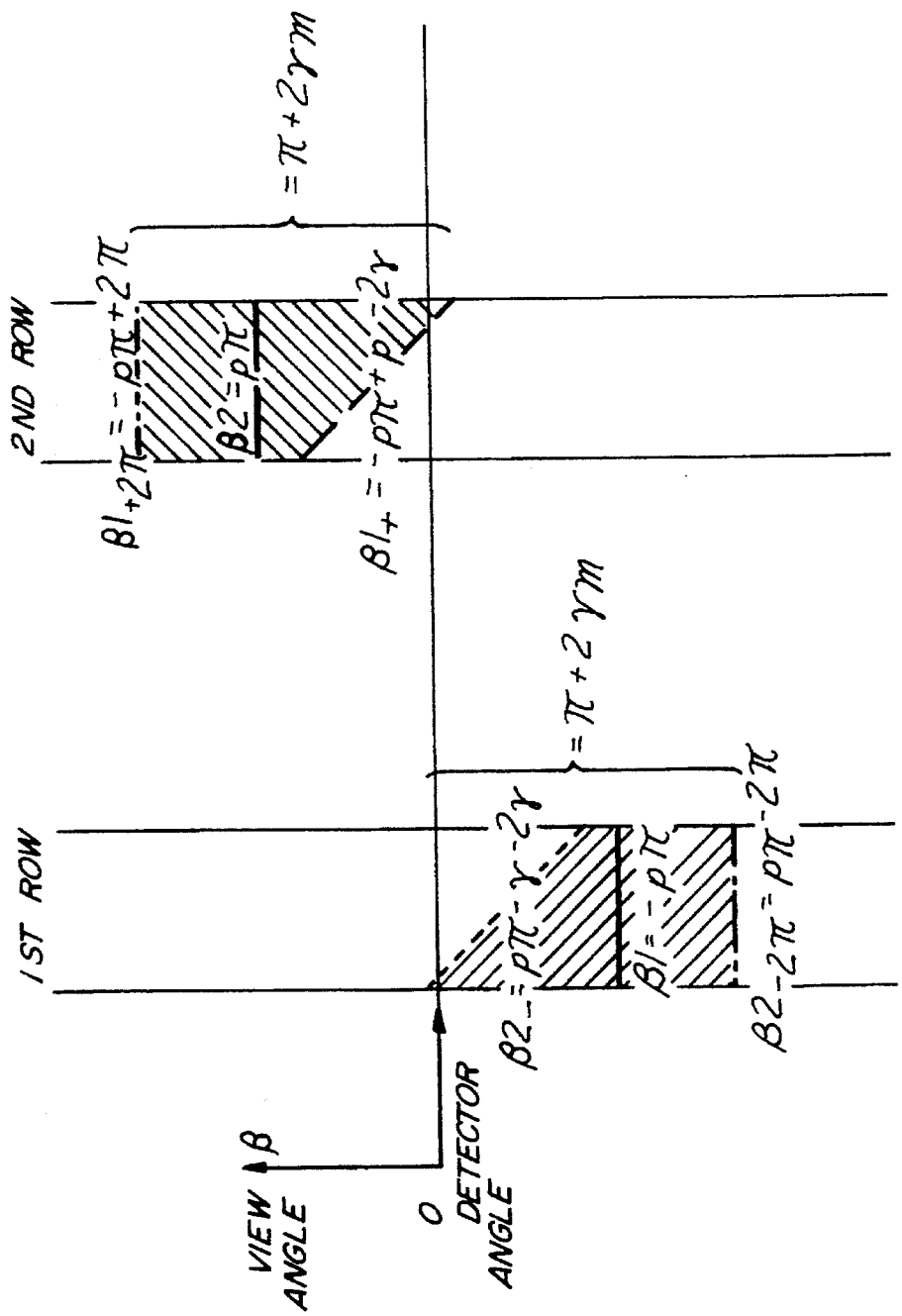
FIG. 7 illustrates two data planes and selected data regions utilized for constructing an image slice for the first set of conditions.

The regions in the data planes defined by the weighting function are illustrated in FIGS. 6 and 7. The shaded areas in FIG. 7 represent the data from each data plane used to reconstruct an image slice in accordance with the present invention. For a fan angle $2\gamma_m = \pi/4$, the operable range for this image reconstruction algorithm is $d < s < 8/5 d$.

The weighting function described in Equation 5 is continuous. However, its first derivative is discontinuous at the boundary lines. If necessary, this discontinuity can be eliminated by feathering a few channels (~10 channels) across the boundary.

Further in accordance with the present invention, and when the table feeding speed s and the detector z spacing, d, satisfy the relation $s > ((2\pi/(\pi - 2\gamma_m))d$, the helical weighting factor for each data set, denoted as W1 $(\beta, \gamma)$ and W2 $(\beta, \gamma)$, are:

$$W1(\beta,\gamma) = \begin{cases} 0 & \beta \leq \beta2_- \\ \dfrac{\beta - \beta2_-}{\beta1 - \beta2_-} & \beta2_- < \beta \leq \beta1 \\ \dfrac{\beta - \beta2}{\beta1 - \beta2} & \beta1 < \beta < \beta2 \\ 0 & \beta \geq \beta2 \end{cases} \tag{6}$$

-continued $$W2(\beta,\gamma) = \begin{cases} 0 & \beta \leq \beta 1 \\ \dfrac{\beta - \beta 1}{\beta 2 - \beta 1} & \beta 1 < \beta < \beta 2 \\ \dfrac{\beta - \beta 1_+}{\beta 2 - \beta 1_+} & \beta 2 \leq \beta < \beta 1_+ \\ 0 & \beta \geq \beta 1_+ \end{cases}$$

Figure 8:
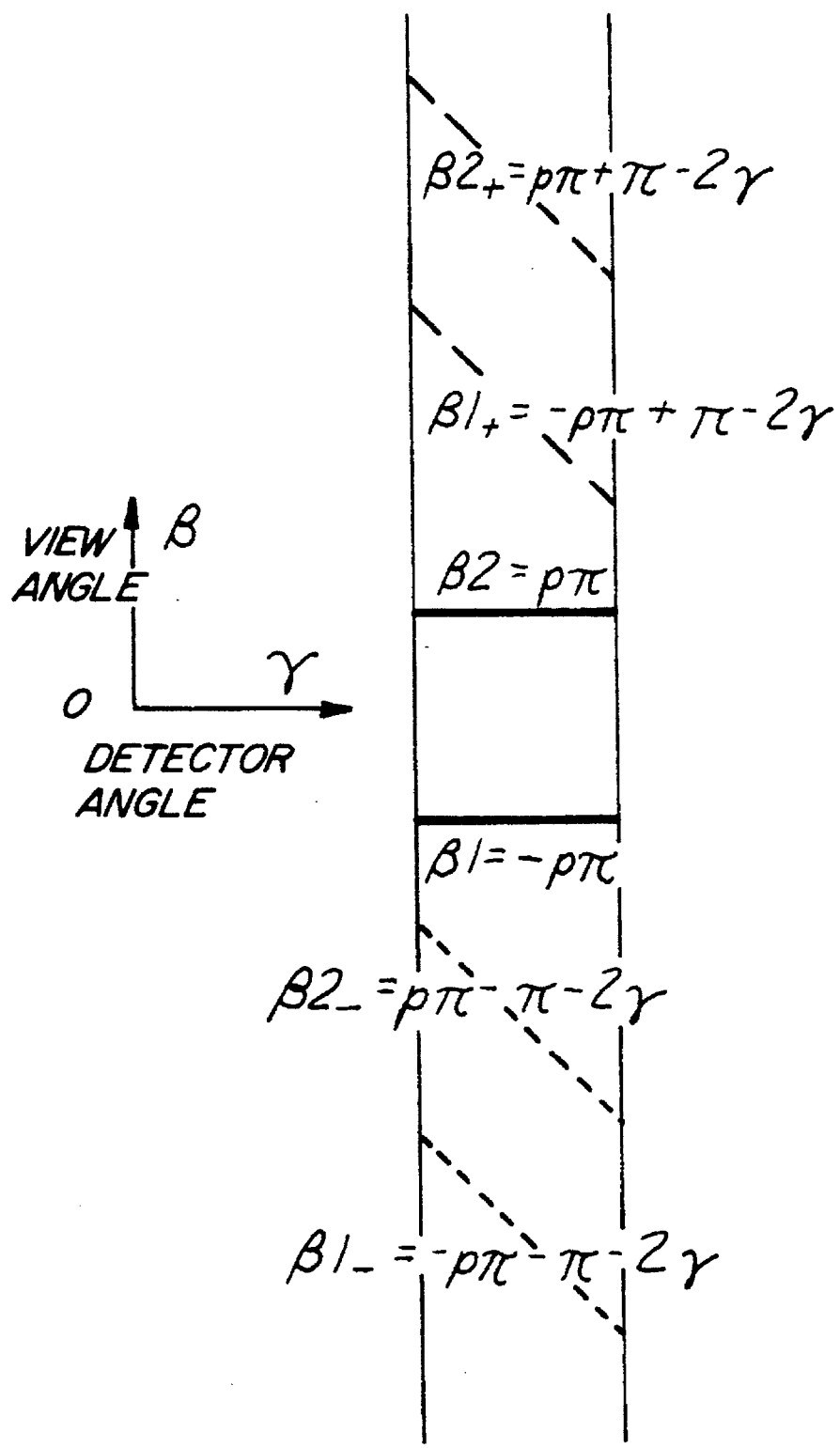
FIG. 8 illustrates a data plane and various data regions for a second set of conditions.
Figure 9:
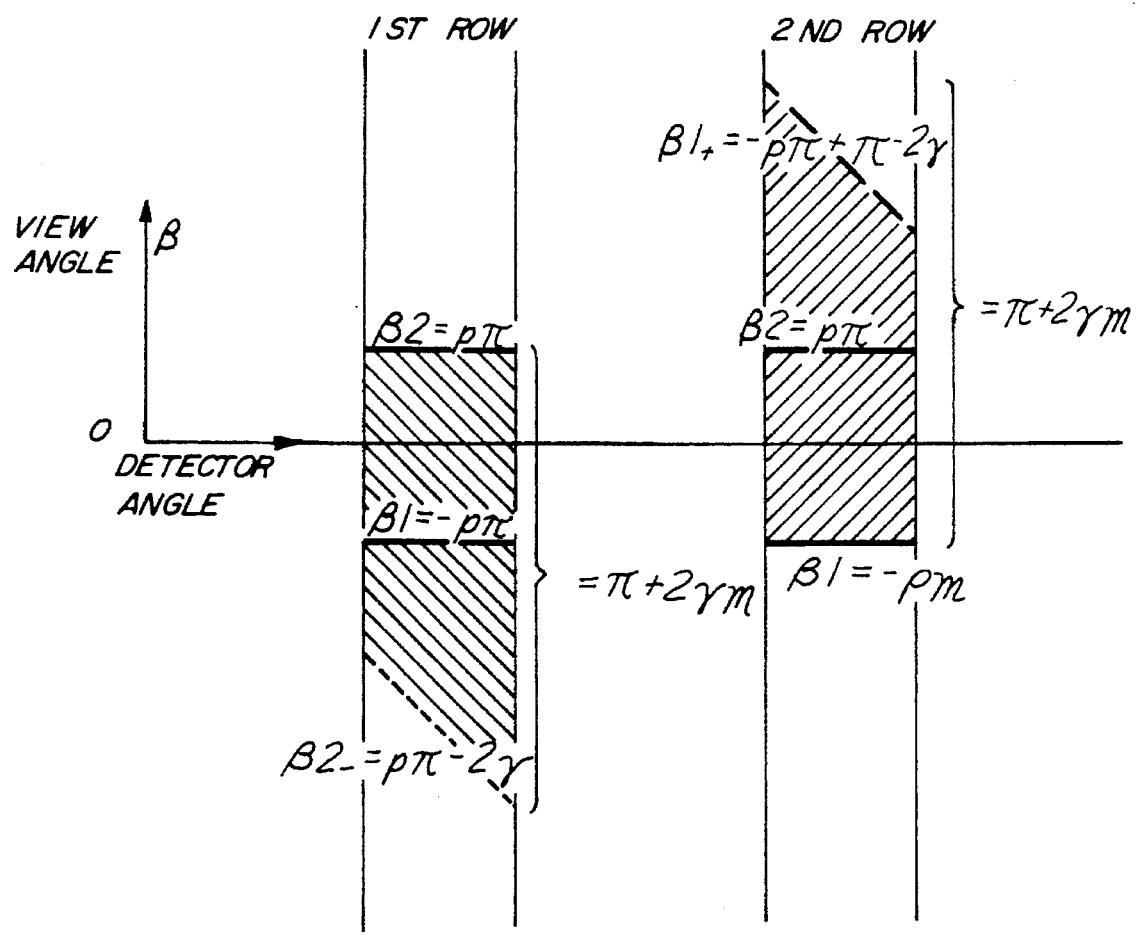
FIG. 9 illustrates two data planes and selected data regions utilized for constructing an image slice for the second set of conditions.

The regions in the data planes defined by the weighting function are illustrated in FIGS. 8 and 9. The shaded areas in FIG. 9 represent the data from each data plane used to reconstruct an image slice in accordance with the present invention. The weighting function described in Equation 6 is continuous, and its first derivative is discontinuous at the boundary lines. If necessary, this discontinuity can be eliminated by feathering a few channels (~10 channels) across the boundary. For a fan angle $2\gamma_m = \pi/4$, the operable range for this image reconstruction algorithm is $s > (\frac{5}{3})d$.

Once weighted to create weighted projection data arrays 56 and 60, and to reduce processing time, the projections from the same gantry (view) angle but from different detector rows can be combined prior to filtration and back projection. Some projection views in data row 1 are 360 degrees apart of the corresponding projection views in data row 2. These view pairs can be further combined prior to the filtration to eliminate any unnecessary increase in processing load.

With respect to both algorithms described above, 2 ($\pi+2\gamma_m$) worth of projection data needs to be preprocessed to reconstruct one slice. Compared to the amount of data needed to reconstruct an image in conventional scans (both axial and helical), the preprocessing load increased by 1.25 times in this dual beam helical scan.

The projection data required for reconstructing adjacent slices can be identified by vertically shifting the origin of the view angle $\beta$ to align to a new slice to be reconstructed. In most cases, there are significant overlaps between the data for one slice and for the adjacent slices in each data set. Prior to weighting, the preprocessing is not slice-position-dependent. Thus, preprocessing (without helical weighting) results can be stored in buffers for future reuse. This greatly reduces the preprocessing load in most cases, especially in retrospective reconstruction.

If the desired slice profile is thicker than the profiles supported by the data and reconstruction algorithms described above, a thicker slice can be derived by summing multiple thin slices within the desired slice profile. If the multiple thin slices, by themselves, are not of interest, the intermediate step of reconstructing multiple thin slices can be bypassed by performing the corresponding summation early in the projection domain. This reduces the computation load and the image storage load. The resultant weighting functions can be derived by summing corresponding shifted versions of the data planes.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. The present invention, however, may be used with many other CT systems including "fourth generation" systems wherein the detector is a full-ring stationary detector and only the x-ray source rotates with the gantry. Accordingly, the spirit and scope of the invention are to be limited only by the terms of the appended claims.

What is claimed is:

1. A system for producing a tomographic image of an object from projection data acquired in a helical scan, said system generating data from a pair of x-ray fan beams disposed along a z axis, said system comprising a data acquisition system configured to:
   (a) create projection data arrays corresponding to the data obtained from each of the x-ray fan beams;
   (b) apply a weighting function to each of the projection data arrays generated in step (a) to generate respective weighted projection data arrays, the weighting function applied being:
   (i) if the table feeding speed s and detector z spacing, d, satisfy the relation $d<s<(2\pi/(\pi+2\gamma_m))d$, the helical weighting factors to be applied for each data set, denoted as W1 ($\beta,\gamma$) and W2 ($\beta, \gamma$), are:

$$W1(\beta,\gamma) = \begin{cases} 0 & \beta \leq \beta 2_{-2\pi} \\ \dfrac{\beta - \beta 2_{-2\pi}}{\beta 1 - \beta 2_{-2\pi}} & \beta 2_{-2\pi} < \beta \leq \beta 1 \\ \dfrac{\beta - \beta 2_-}{\beta 1 - \beta 2_-} & \beta 1 < \beta < \beta 2_- \\ 0 & \beta \geq \beta 2_- \end{cases}$$

$$W2(\beta,\gamma) = \begin{cases} 0 & \beta \leq \beta 1_+ \\ \dfrac{\beta - \beta 1_+}{\beta 2 - \beta 1_-} & \beta 1_+ < \beta < \beta 2 \\ \dfrac{\beta - \beta 1_{+2\pi}}{\beta 2 - \beta 1_{+2\pi}} & \beta 2 \leq \beta < \beta 1_{+2\pi} \\ 0 & \beta \geq \beta 1_{+2\pi} \end{cases}$$

(ii) if the table feeding speed s and detector z spacing, d, satisfy the relation $s>((2\pi/(\pi-2\gamma_m))d$, the helical weighting factors to be applied for each data set, denoted as W1 ($\beta, \gamma$) and W2 ($\beta, \gamma$), are:

$$W1(\beta,\gamma) = \begin{cases} 0 & \beta \leq \beta 2_- \\ \dfrac{\beta - \beta 2_-}{\beta 1 - \beta 2_-} & \beta 2_- < \beta \leq \beta 1 \\ \dfrac{\beta - \beta 2}{\beta 1 - \beta 2} & \beta 1 < \beta < \beta 2 \\ 0 & \beta \geq \beta 2 \end{cases}$$

$$W2(\beta,\gamma) = \begin{cases} 0 & \beta \leq \beta 1 \\ \dfrac{\beta - \beta 1}{\beta 2 - \beta 1} & \beta 1 < \beta < \beta 2 \\ \dfrac{\beta - \beta 1_+}{\beta 2 - \beta 1_+} & \beta 2 \leq \beta < \beta 1_+ \\ 0 & \beta \geq \beta 1_+, \end{cases}$$

(c) from the projection data arrays generated in step (b), generate image data arrays to be used to construct a slice image.

2. A system in accordance with claim 1 wherein generating image data arrays comprises the step of performing filtration and back projection on each weighted projection data array.

3. A system in accordance with claim 2 wherein prior to performing filtration and back projection, and the data arrays from a same gantry angle but from different detector rows are combined.

4. A system in accordance with claim 3 wherein if a projection view in a first data row are three hundred and sixty degrees from the a projection view in a second data row, combining the views prior to filtration and back projection.

5. A system in accordance with claim 1 wherein prior to applying a weighting function to each of the projection data arrays, storing the data in a system memory for reconstructing consecutive slices.

6. A system in accordance with claim 1 wherein the data acquisition system is further configured to sum multiple thin slices within a desired slice profile if the desired slice profile is thicker than profiles supported by the data array.

7. A method for producing a tomographic image of an object from projection data acquired in a helical scan, the system generating data from a pair of x-ray fan beams disposed along a z axis, the table feeding speed s and detector z spacing, d, satisfying the relation $d<s<(2\pi/(\pi+2\gamma_m))d$, said method comprising the steps of:

(a) creating projection data arrays corresponding to the data obtained from each of the x-ray fan beams;

(b) applying a weighting function to each of the projection data arrays generated in step (a) to generate respective weighted projection data arrays, the weighting factors to be applied for each data set, denoted as $W1(\beta, \gamma)$ and $W2(\beta, \gamma)$, being:

$$W1(\beta,\gamma) = \begin{cases} 0 & \beta \leq \beta 2_{-2\pi} \\ \dfrac{\beta - \beta 2_{-2\pi}}{\beta 1 - \beta 2_{-2\pi}} & \beta 2_{-2\pi} < \beta \leq \beta 1 \\ \dfrac{\beta - \beta 2}{\beta 1 - \beta 2_{-}} & \beta 1 < \beta < \beta 2_{-} \\ 0 & \beta \geq \beta 2_{-} \end{cases}$$

$$W2(\beta,\gamma) = \begin{cases} 0 & \beta \leq \beta 1_{+} \\ \dfrac{\beta - \beta 1_{+}}{\beta 2 - \beta 1_{+}} & \beta 1_{+} < \beta < \beta 2 \\ \dfrac{\beta - \beta 1_{+2\pi}}{\beta 2 - \beta 1_{+2\pi}} & \beta 2 \leq \beta < \beta 1_{+2\pi} \\ 0 & \beta \geq \beta 1_{+2\pi} \end{cases}$$

(c) from the projection data arrays generated in step (b), generating image data arrays to be used to construct a slice image.

8. A method in accordance with claim 7 wherein generating image data arrays comprises the step of performing filtration and back projection on each weighted projection data array.

9. A method in accordance with claim 8 wherein prior to performing filtration and back projection, and the data arrays from a same gantry angle but from different detector rows are combined.

10. A method in accordance with claim 9 wherein if a projection view in a first data row are three hundred and sixty degrees from the a projection view in a second data row, combining the views prior to performing filtration and back projection.

11. A method in accordance with claim 8 wherein prior to applying a weighting function to each of the projection data arrays, storing the data in a system memory for reconstructing consecutive slices.

12. A method in accordance with claim 8 wherein the data acquisition system is further configured to sum multiple thin slices within a desired slice profile if the desired slice profile is thicker than profiles supported by the data array.

13. A method for producing a tomographic image of an object from projection data acquired in a helical scan, the system generating data from a pair of x-ray fan beams disposed along a z axis, the table feeding speed s and detector z spacing, d, satisfying the relation $s>((2\pi/(\pi-2\gamma_m))d$, said method comprising the steps of:

(a) creating projection data arrays corresponding to the data obtained from each of the x-ray fan beams;

(b) applying a weighting function to each of the projection data arrays generated in step (a) to generate respective weighted projection data arrays, the weighting factors to be applied for each data set, denoted as $W1(\beta, \gamma)$ and $W2(\beta, \gamma)$, being:

$$W1(\beta,\gamma) = \begin{cases} 0 & \beta \leq \beta 2_{-} \\ \dfrac{\beta - \beta 2}{\beta 1 - \beta 2_{-}} & \beta 2_{-} < \beta \leq \beta 1 \\ \dfrac{\beta - \beta 2}{\beta 1 - \beta 2} & \beta 1 < \beta < \beta 2 \\ 0 & \beta \geq \beta 2 \end{cases}$$

$$W2(\beta,\gamma) = \begin{cases} 0 & \beta \leq \beta 1 \\ \dfrac{\beta - \beta 1}{\beta 2 - \beta 1} & \beta 1 < \beta < \beta 2 \\ \dfrac{\beta - \beta 1_{+}}{\beta 2 - \beta 1_{+}} & \beta 2 \leq \beta < \beta 1_{+} \\ 0 & \beta \geq \beta 1_{+} \end{cases}$$

(c) from the projection data arrays generated in step (b), generating image data arrays to be used to construct a slice image.

14. A method in accordance with claim 13 wherein generating image data arrays comprises the step of performing filtration and back projection on each weighted projection data array.

15. A method in accordance with claim 14 wherein prior to performing filtration and back projection, and the data arrays from a same gantry angle but from different detector rows are combined.

16. A method in accordance with claim 15 wherein if a projection view in a first data row are three hundred and sixty degrees from the a projection view in a second data row, combining the views prior to filtration and back projection.

17. A method in accordance with claim 13 wherein prior to applying a weighting function to each of the projection data arrays, storing the data in a system memory for reconstructing consecutive slices.

18. A method in accordance with claim 13 wherein the data acquisition system is further configured to sum multiple thin slices within a desired slice profile if the desired slice profile is thicker than profiles supported by the data array.

* * * * *

UNITED STATES PATENT AND TRADEMARK OFFICE
CERTIFICATE OF CORRECTION

PATENT NO. : 5,513,236
DATED : April 30, 1996
INVENTOR(S) : Hui Hu

It is certified that error appears in the above-indentified patent and that said Letters Patent is hereby corrected as shown below:

On the title page, under item [19], change "Hui" to --Hu--.
On the title page, item [75], change "Hu Hui" to --Hui Hu--.

Signed and Sealed this

Third Day of September, 1996

Attest:

BRUCE LEHMAN

Attesting Officer

Commissioner of Patents and Trademarks